United States Patent
Artsyukhovich et al.

(10) Patent No.: US 9,233,021 B2
(45) Date of Patent: *Jan. 12, 2016

(54) PHACOEMULSIFICATION HOOK TIP

(71) Applicant: Alcon Research, Ltd., Fort Worth, TX (US)

(72) Inventors: Alexander N. Artsyukhovich, Irvine, CA (US); Mikhail Boukhny, Laguna Niguel, CA (US); James Y. Chon, Irvine, CA (US); Ramon Carsola Dimalanta, Jr., Trabuco Canyon, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/062,254

(22) Filed: Oct. 24, 2013

(65) Prior Publication Data

US 2014/0052141 A1    Feb. 20, 2014

Related U.S. Application Data

(63) Continuation of application No. 12/496,220, filed on Jul. 1, 2009, now Pat. No. 8,623,040.

(51) Int. Cl.
*A61F 9/007* (2006.01)
*A61B 17/32* (2006.01)

(52) U.S. Cl.
CPC ..... *A61F 9/00745* (2013.01); *A61B 17/320068* (2013.01)

(58) Field of Classification Search
CPC .................. A61F 9/00745; A61B 17/320068
USPC ........... 606/107, 166, 167, 169, 171; 604/22, 604/272

See application file for complete search history.

(56) References Cited

U.S. PATENT DOCUMENTS

| 1,312,408 A | 2/1885 | Wackerhagen |
| 1,397,395 A | 11/1921 | Bixler |

(Continued)

FOREIGN PATENT DOCUMENTS

| AU | 2003241752 A1 | 9/2003 |
| AU | 2011202357 A1 | 6/2011 |

(Continued)

OTHER PUBLICATIONS

"Phacoemulsification Tip Technology Guide," Alcon brochure, Dec. 2009, 8 pages.

(Continued)

*Primary Examiner* — Kathleen Holwerda

(57) ABSTRACT

In various embodiments, a phacoemulsification cutting tip with a straight shaft and an angled portion off of the straight shaft may include a hook on the angled portion to move an axis of rotation of the cutting tip closer to alignment with an extended centerline of the shaft. The cutting tip may be configured to torsionally rotate back and forth on an axis perpendicular to a centerline of the shaft (e.g., rotation around a y-axis). In some embodiments, lateral vibrations (e.g., side to side along an x-axis or z-axis perpendicular to the y-axis) that result from torsional rotation around the y-axis in a cutting tip without the hook may be reduced through use of the hook to balance the otherwise eccentrically weighted hook.

14 Claims, 7 Drawing Sheets

(56) References Cited

U.S. PATENT DOCUMENTS

| | | |
|---|---|---|
| 2,070,281 A | 2/1937 | Leggiadro |
| 2,874,470 A | 2/1959 | Richards |
| 2,990,616 A | 7/1961 | Balamuth et al. |
| RE25,033 E | 8/1961 | Balamuth et al. |
| 3,053,124 A | 9/1962 | Balamuth et al. |
| 3,086,288 A | 4/1963 | Balamuth et al. |
| 3,133,351 A | 5/1964 | Von Seggern |
| 3,257,721 A | 6/1966 | Joens et al. |
| 3,433,226 A | 3/1969 | Boyd |
| 3,513,848 A | 5/1970 | Winston |
| 3,518,766 A * | 7/1970 | Emanuel ............... 433/86 |
| 3,526,219 A | 9/1970 | Balamuth |
| 3,546,498 A | 12/1970 | McMaster et al. |
| 3,565,062 A | 2/1971 | Kuris |
| 3,589,363 A | 6/1971 | Banko |
| 3,601,126 A | 8/1971 | Estes |
| 3,610,080 A | 10/1971 | Kuris |
| 3,657,056 A | 4/1972 | Winston et al. |
| 3,693,613 A | 9/1972 | Kelman |
| 3,703,037 A | 11/1972 | Robinson |
| 3,812,855 A | 5/1974 | Banko |
| 3,812,858 A | 5/1974 | Oringer |
| 3,830,240 A | 8/1974 | Antonevich et al. |
| 3,857,387 A | 12/1974 | Shock |
| 3,861,391 A | 1/1975 | Antonevich et al. |
| 3,888,004 A | 6/1975 | Coleman |
| 3,902,495 A | 9/1975 | Weiss et al. |
| 3,930,173 A | 12/1975 | Banko |
| 3,930,505 A | 1/1976 | Wallach |
| 3,937,990 A | 2/1976 | Winston |
| 3,942,519 A | 3/1976 | Shock |
| 3,943,932 A | 3/1976 | Woo |
| 3,952,732 A | 4/1976 | Shock |
| 3,956,826 A | 5/1976 | Perdreaux, Jr. |
| 3,964,487 A | 6/1976 | Judson |
| 3,990,452 A | 11/1976 | Murry et al. |
| 4,012,647 A | 3/1977 | Balamuth et al. |
| 4,024,467 A | 5/1977 | Andrews et al. |
| 4,024,866 A | 5/1977 | Wallach |
| 4,063,557 A | 12/1977 | Wuchinich et al. |
| 4,114,623 A | 9/1978 | Meinke et al. |
| 4,126,137 A | 11/1978 | Archibald |
| 4,136,700 A | 1/1979 | Broadwin et al. |
| 4,156,187 A | 5/1979 | Murry et al. |
| 4,168,707 A | 9/1979 | Douvas et al. |
| 4,169,984 A | 10/1979 | Parisi |
| 4,184,510 A | 1/1980 | Murry et al. |
| 4,223,676 A | 9/1980 | Wuchinich et al. |
| 4,246,902 A | 1/1981 | Martinez |
| 4,248,232 A | 2/1981 | Engelbrecht et al. |
| 4,283,175 A | 8/1981 | Nash |
| 4,406,284 A | 9/1983 | Banko |
| 4,417,578 A | 11/1983 | Banko |
| 4,493,694 A | 1/1985 | Wuchinich |
| 4,496,342 A | 1/1985 | Banko |
| 4,504,264 A | 3/1985 | Kelman |
| 4,508,532 A | 4/1985 | Drews et al. |
| 4,515,583 A | 5/1985 | Sorich |
| 4,526,571 A | 7/1985 | Wuchinich |
| 4,530,359 A | 7/1985 | Helfgott et al. |
| 4,561,438 A | 12/1985 | Bonnet et al. |
| 4,589,415 A | 5/1986 | Haaga |
| 4,590,935 A | 5/1986 | Ranalli |
| 4,609,368 A | 9/1986 | Dotson, Jr. |
| 4,634,419 A | 1/1987 | Kreizman et al. |
| 4,651,280 A | 3/1987 | Chang et al. |
| 4,658,819 A | 4/1987 | Harris et al. |
| 4,676,243 A | 6/1987 | Clayman |
| 4,697,117 A | 9/1987 | Mishiro |
| 4,705,500 A | 11/1987 | Reimels et al. |
| 4,705,980 A | 11/1987 | Mishiro |
| 4,706,669 A | 11/1987 | Schlegel |
| 4,712,544 A | 12/1987 | Ensslin |
| 4,739,759 A | 4/1988 | Rexroth et al. |
| 4,750,488 A | 6/1988 | Wuchinich et al. |
| 4,750,902 A | 6/1988 | Wuchinich et al. |
| 4,766,897 A | 8/1988 | Smirmaul |
| 4,770,654 A | 9/1988 | Rogers et al. |
| 4,793,346 A | 12/1988 | Mindich |
| 4,812,697 A | 3/1989 | Mishiro |
| 4,816,018 A | 3/1989 | Parisi |
| 4,827,911 A | 5/1989 | Broadwin et al. |
| 4,832,683 A | 5/1989 | Idemoto et al. |
| 4,869,715 A | 9/1989 | Sherburne |
| 4,869,716 A | 9/1989 | Smirmaul |
| 4,885,499 A | 12/1989 | Ueha et al. |
| 4,911,161 A * | 3/1990 | Schechter ............... 606/107 |
| 4,920,954 A | 5/1990 | Alliger et al. |
| 4,922,902 A | 5/1990 | Wuchinich et al. |
| 4,950,272 A | 8/1990 | Smirmaul |
| 4,961,424 A | 10/1990 | Kubota et al. |
| 4,965,482 A | 10/1990 | Ohnishi et al. |
| 4,969,885 A | 11/1990 | Farin |
| 4,974,581 A | 12/1990 | Wiksell |
| 4,989,583 A | 2/1991 | Hood |
| 4,989,588 A | 2/1991 | Kubota et al. |
| 4,992,048 A | 2/1991 | Goof |
| 5,019,083 A | 5/1991 | Klapper et al. |
| 5,026,387 A | 6/1991 | Thomas |
| 5,047,008 A | 9/1991 | de Juan, Jr. et al. |
| 5,047,043 A | 9/1991 | Kubota et al. |
| 5,062,827 A | 11/1991 | Wiksell |
| 5,084,012 A | 1/1992 | Kelman |
| 5,094,617 A | 3/1992 | Carr |
| 5,112,300 A | 5/1992 | Ureche |
| 5,112,339 A | 5/1992 | Zelman |
| 5,116,343 A | 5/1992 | Ams et al. |
| 5,116,352 A | 5/1992 | Schnepp-Pesch et al. |
| 5,139,509 A | 8/1992 | Fischer et al. |
| 5,151,085 A | 9/1992 | Sakurai et al. |
| 5,154,694 A | 10/1992 | Kelman |
| 5,154,696 A | 10/1992 | Shearing |
| 5,160,317 A | 11/1992 | Costin |
| 5,176,677 A | 1/1993 | Wuchinich |
| 5,180,363 A | 1/1993 | Idemoto et al. |
| 5,188,102 A | 2/1993 | Idemoto et al. |
| 5,188,589 A | 2/1993 | Wypych et al. |
| 5,205,817 A | 4/1993 | Idemoto et al. |
| 5,213,569 A | 5/1993 | Davis |
| 5,217,465 A | 6/1993 | Steppe |
| 5,221,282 A | 6/1993 | Wuchinich |
| 5,222,937 A | 6/1993 | Kagawa |
| 5,222,959 A | 6/1993 | Anis |
| 5,242,385 A | 9/1993 | Strukel |
| 5,248,296 A | 9/1993 | Alliger |
| 5,267,954 A | 12/1993 | Nita |
| 5,269,297 A | 12/1993 | Weng et al. |
| 5,279,547 A | 1/1994 | Costin |
| 5,304,115 A | 4/1994 | Pflueger et al. |
| 5,312,329 A | 5/1994 | Beaty et al. |
| 5,318,570 A | 6/1994 | Hood et al. |
| 5,322,055 A | 6/1994 | Davison et al. |
| 5,331,951 A | 7/1994 | Kepley |
| 5,342,293 A | 8/1994 | Zanger |
| 5,359,996 A | 11/1994 | Hood |
| 5,364,405 A | 11/1994 | Zaleski |
| 5,382,228 A | 1/1995 | Nita et al. |
| 5,391,144 A | 2/1995 | Sakurai et al. |
| 5,397,293 A | 3/1995 | Alliger et al. |
| 5,397,301 A | 3/1995 | Pflueger et al. |
| 5,413,578 A | 5/1995 | Zahedi |
| 5,417,654 A | 5/1995 | Kelman |
| 5,431,664 A | 7/1995 | Ureche et al. |
| 5,451,220 A | 9/1995 | Ciervo |
| 5,451,230 A | 9/1995 | Steinert |
| 5,469,011 A | 11/1995 | Safabakhsh |
| 5,480,379 A | 1/1996 | La Rosa |
| 5,507,738 A | 4/1996 | Ciervo |
| 5,514,151 A | 5/1996 | Fogarty et al. |
| 5,520,633 A | 5/1996 | Costin |
| 5,527,273 A | 6/1996 | Manna et al. |
| 5,531,597 A | 7/1996 | Foulkes et al. |
| 5,569,188 A | 10/1996 | Mackool |
| 5,591,127 A | 1/1997 | Barwick, Jr. et al. |

(56) References Cited

U.S. PATENT DOCUMENTS

| | | | |
|---|---|---|---|
| 5,634,912 | A | 6/1997 | Injev |
| 5,653,724 | A | 8/1997 | Imonti |
| 5,669,922 | A | 9/1997 | Hood |
| 5,676,649 | A | 10/1997 | Boukhny et al. |
| 5,688,235 | A | 11/1997 | Sakurai et al. |
| 5,690,641 | A | 11/1997 | Sorensen et al. |
| 5,700,240 | A | 12/1997 | Barwick, Jr. et al. |
| 5,722,945 | A | 3/1998 | Anis et al. |
| 5,725,495 | A | 3/1998 | Strukel et al. |
| 5,728,130 | A | 3/1998 | Ishikawa et al. |
| 5,733,256 | A | 3/1998 | Costin |
| 5,743,871 | A | 4/1998 | Strukel et al. |
| 5,746,756 | A | 5/1998 | Bromfield et al. |
| 5,766,146 | A | 6/1998 | Barwick, Jr. |
| 5,776,155 | A | 7/1998 | Beaupre et al. |
| 5,800,448 | A | 9/1998 | Banko |
| 5,808,396 | A | 9/1998 | Boukhny |
| 5,810,859 | A | 9/1998 | DiMatteo et al. |
| 5,817,036 | A | 10/1998 | Anthony et al. |
| 5,819,571 | A | 10/1998 | Johnson |
| 5,825,118 | A | 10/1998 | Okazaki |
| 5,865,790 | A | 2/1999 | Bair |
| 5,879,364 | A | 3/1999 | Bromfield et al. |
| 5,897,523 | A | 4/1999 | Wright et al. |
| 5,904,690 | A | 5/1999 | Middleman et al. |
| 5,921,999 | A | 7/1999 | Dileo |
| 5,935,096 | A | 8/1999 | Barrett |
| 5,938,633 | A | 8/1999 | Beaupre |
| 5,938,677 | A | 8/1999 | Boukhny et al. |
| 5,941,887 | A | 8/1999 | Steen et al. |
| 5,944,737 | A | 8/1999 | Tsonton et al. |
| 5,968,058 | A | 10/1999 | Richter et al. |
| 5,971,949 | A | 10/1999 | Levin et al. |
| 5,979,494 | A | 11/1999 | Perkins et al. |
| 5,989,275 | A | 11/1999 | Estabrook et al. |
| 5,993,409 | A | 11/1999 | Maaskamp |
| 6,013,046 | A | 1/2000 | Maaskamp et al. |
| 6,013,048 | A | 1/2000 | Podany et al. |
| 6,024,750 | A | 2/2000 | Mastri et al. |
| 6,027,515 | A | 2/2000 | Cimino |
| 6,028,387 | A | 2/2000 | Boukhny |
| 6,039,715 | A | 3/2000 | Mackool |
| 6,053,906 | A | 4/2000 | Honda et al. |
| 6,056,735 | A | 5/2000 | Okada et al. |
| 6,063,050 | A | 5/2000 | Manna et al. |
| 6,077,285 | A | 6/2000 | Boukhny |
| 6,083,193 | A | 7/2000 | Kadziauskas et al. |
| 6,159,175 | A | 12/2000 | Strukel et al. |
| 6,171,265 | B1 | 1/2001 | Novak et al. |
| 6,175,180 | B1 | 1/2001 | Angelini et al. |
| 6,179,805 | B1 | 1/2001 | Sussman et al. |
| 6,179,808 | B1 | 1/2001 | Boukhny et al. |
| 6,193,683 | B1 | 2/2001 | Ludin et al. |
| 6,206,844 | B1 | 3/2001 | Reichel et al. |
| 6,217,543 | B1 | 4/2001 | Anis et al. |
| 6,228,046 | B1 | 5/2001 | Brisken |
| 6,238,386 | B1 | 5/2001 | Muller et al. |
| 6,241,700 | B1 | 6/2001 | Leukanech |
| 6,241,703 | B1 | 6/2001 | Levin et al. |
| 6,251,110 | B1 | 6/2001 | Wampler |
| 6,254,622 | B1 | 7/2001 | Hood |
| 6,256,859 | B1 | 7/2001 | Stoddard et al. |
| 6,258,053 | B1 | 7/2001 | Mackool |
| 6,261,283 | B1 | 7/2001 | Morgan et al. |
| 6,261,297 | B1 | 7/2001 | Kadziauskas et al. |
| 6,278,218 | B1 | 8/2001 | Madan et al. |
| 6,280,407 | B1 | 8/2001 | Manna et al. |
| 6,283,974 | B1 | 9/2001 | Alexander |
| 6,283,981 | B1 | 9/2001 | Beaupre |
| 6,309,400 | B2 | 10/2001 | Beaupre |
| 6,315,755 | B1 | 11/2001 | Sussman |
| 6,325,811 | B1 | 12/2001 | Messerly |
| 6,328,751 | B1 | 12/2001 | Beaupre |
| 6,352,519 | B1 | 3/2002 | Anis |
| 6,394,974 | B1 | 5/2002 | Kadziauskas et al. |
| 6,400,648 | B1 | 6/2002 | Heijnskijk et al. |
| 6,402,769 | B1 * | 6/2002 | Boukhny ............... 606/169 |
| 6,423,074 | B1 | 7/2002 | Chen |
| 6,428,501 | B1 | 8/2002 | Reynard |
| 6,432,118 | B1 | 8/2002 | Messerly |
| 6,436,115 | B1 | 8/2002 | Beaupre |
| 6,458,143 | B1 | 10/2002 | Sugai |
| 6,468,286 | B2 | 10/2002 | Mastri et al. |
| 6,475,224 | B1 | 11/2002 | Pantages et al. |
| 6,478,766 | B1 | 11/2002 | Chon |
| 6,491,661 | B1 | 12/2002 | Boukhny et al. |
| 6,491,708 | B2 | 12/2002 | Madan et al. |
| 6,494,868 | B2 | 12/2002 | Amar |
| 6,514,267 | B2 | 2/2003 | Jewett |
| 6,533,750 | B2 | 3/2003 | Sutton et al. |
| 6,551,337 | B1 | 4/2003 | Rabiner et al. |
| 6,561,983 | B2 | 5/2003 | Cronin et al. |
| 6,585,745 | B2 | 7/2003 | Cimino |
| 6,592,541 | B1 | 7/2003 | Kurwa |
| 6,602,193 | B2 | 8/2003 | Chon |
| 6,605,054 | B2 | 8/2003 | Rockley |
| 6,629,948 | B2 | 10/2003 | Rockley et al. |
| 6,660,017 | B2 | 12/2003 | Beaupre |
| 6,679,899 | B2 | 1/2004 | Wiener et al. |
| 6,682,544 | B2 | 1/2004 | Mastri et al. |
| 6,699,212 | B1 | 3/2004 | Kadziauskas et al. |
| 6,736,835 | B2 | 5/2004 | Pellegrino et al. |
| 6,752,815 | B2 | 6/2004 | Beaupre |
| 6,773,444 | B2 | 8/2004 | Messerly |
| 6,780,165 | B2 | 8/2004 | Kadziauskas et al. |
| 6,811,553 | B2 | 11/2004 | Anthone |
| 6,887,240 | B1 | 5/2005 | Lands et al. |
| 6,893,434 | B2 | 5/2005 | Fenton et al. |
| 6,898,536 | B2 | 5/2005 | Wiener et al. |
| 6,923,421 | B2 | 8/2005 | Raftis |
| 6,939,317 | B2 | 9/2005 | Zacharias |
| 6,955,680 | B2 * | 10/2005 | Satou et al. ............ 606/169 |
| 6,976,969 | B2 | 12/2005 | Messerly |
| 6,984,220 | B2 | 1/2006 | Wuchinich |
| 7,014,629 | B2 | 3/2006 | Mackool |
| 7,018,389 | B2 | 3/2006 | Camerlengo |
| 7,019,234 | B1 | 3/2006 | Mezhinsky et al. |
| 7,037,296 | B2 | 5/2006 | Kadziauskas et al. |
| 7,163,548 | B2 | 1/2007 | Stulen et al. |
| 7,185,555 | B2 | 3/2007 | Peterson et al. |
| 7,229,455 | B2 | 6/2007 | Sakurai et al. |
| 7,285,895 | B2 | 10/2007 | Beaupre |
| 7,297,137 | B2 | 11/2007 | Gordon et al. |
| 7,300,446 | B2 | 11/2007 | Beaupre |
| 7,316,664 | B2 | 1/2008 | Kadziauskas et al. |
| 7,335,997 | B2 | 2/2008 | Wiener |
| 7,374,552 | B2 | 5/2008 | Wuchinich |
| 7,443,296 | B2 | 10/2008 | Mezhinsky et al. |
| 7,479,148 | B2 | 1/2009 | Beaupre |
| 7,485,106 | B2 | 2/2009 | Kadziauskas et al. |
| 7,530,986 | B2 | 5/2009 | Beaupre |
| 7,572,242 | B2 | 8/2009 | Boukhny |
| 7,604,609 | B2 | 10/2009 | Jervis |
| 7,621,930 | B2 | 11/2009 | Houser |
| 7,625,388 | B2 | 12/2009 | Boukhny et al. |
| 7,645,255 | B2 | 1/2010 | Gordon et al. |
| 7,645,256 | B2 | 1/2010 | Boukhny et al. |
| 7,651,490 | B2 | 1/2010 | Boukhny et al. |
| 7,713,202 | B2 | 5/2010 | Boukhny et al. |
| 7,758,538 | B2 | 7/2010 | Boukhny et al. |
| 7,758,600 | B2 | 7/2010 | Beaupre |
| 7,762,979 | B2 | 7/2010 | Wuchinich |
| 7,794,414 | B2 | 9/2010 | Rabiner et al. |
| 7,821,143 | B2 | 10/2010 | Wiener |
| 8,016,843 | B2 * | 9/2011 | Escaf ............... 606/166 |
| 8,021,381 | B2 | 9/2011 | Beaupre |
| 8,057,498 | B2 | 11/2011 | Robertson |
| 8,058,771 | B2 | 11/2011 | Giordano et al. |
| 8,152,825 | B2 | 4/2012 | Madan et al. |
| 8,172,786 | B2 | 5/2012 | Bouhkny |
| 8,183,022 | B2 | 5/2012 | Steiner |
| 8,241,312 | B2 | 8/2012 | Messerly |
| 8,252,012 | B2 | 8/2012 | Stulen |
| 8,253,303 | B2 | 8/2012 | Giordano et al. |

(56) References Cited

U.S. PATENT DOCUMENTS

| | | | |
|---|---|---|---|
| 8,348,880 B2 | 1/2013 | Messerly et al. | |
| 8,623,040 B2 * | 1/2014 | Artsyukhovich et al. | 606/171 |
| 2001/0025184 A1 | 9/2001 | Messerly | |
| 2001/0027601 A1 | 10/2001 | Stoddard et al. | |
| 2001/0034532 A1 | 10/2001 | Cimino | |
| 2002/0072754 A1 | 6/2002 | Camerlengo | |
| 2002/0128674 A1 | 9/2002 | Beaupre | |
| 2003/0045887 A1 | 3/2003 | Sakurai et al. | |
| 2003/0065263 A1 | 4/2003 | Hare et al. | |
| 2003/0093099 A1 | 5/2003 | Anthone | |
| 2003/0125620 A1 | 7/2003 | Satou et al. | |
| 2003/0164659 A1 | 9/2003 | Iino et al. | |
| 2003/0212331 A1 | 11/2003 | Fenton et al. | |
| 2004/0056220 A1 | 3/2004 | Raftis | |
| 2004/0092800 A1 | 5/2004 | MacKool | |
| 2004/0092922 A1 | 5/2004 | Kadziauskas et al. | |
| 2004/0127887 A1 | 7/2004 | Zinkel | |
| 2004/0127926 A1 | 7/2004 | Beaupre | |
| 2004/0162571 A1 | 8/2004 | Rabiner et al. | |
| 2004/0193104 A1 | 9/2004 | Jervis | |
| 2004/0193121 A1 | 9/2004 | Kadziauskas et al. | |
| 2004/0199192 A1 | 10/2004 | Akahoshi | |
| 2004/0210140 A1 | 10/2004 | Rabiner et al. | |
| 2004/0215127 A1 | 10/2004 | Kadziauskas et al. | |
| 2005/0043671 A1 | 2/2005 | Rockley et al. | |
| 2005/0049546 A1 | 3/2005 | Messerly et al. | |
| 2005/0070939 A1 | 3/2005 | Beaupre | |
| 2005/0075656 A1 | 4/2005 | Beaupre | |
| 2005/0187513 A1 | 8/2005 | Rabiner et al. | |
| 2005/0209621 A1 | 9/2005 | Gordon et al. | |
| 2005/0228425 A1 | 10/2005 | Boukhny et al. | |
| 2005/0234473 A1 | 10/2005 | Zacharias | |
| 2005/0234484 A1 | 10/2005 | Houser et al. | |
| 2005/0261628 A1 | 11/2005 | Boukhny et al. | |
| 2005/0261715 A1 | 11/2005 | Boukhny et al. | |
| 2005/0267504 A1 | 12/2005 | Boukhny et al. | |
| 2005/0273126 A1 | 12/2005 | Beaupre | |
| 2005/0277869 A1 | 12/2005 | Boukhny | |
| 2006/0036180 A1 | 2/2006 | Boukhny et al. | |
| 2006/0041220 A1 | 2/2006 | Boukhny et al. | |
| 2006/0079788 A1 | 4/2006 | Anderson et al. | |
| 2006/0084963 A1 | 4/2006 | Messerly | |
| 2006/0100616 A1 | 5/2006 | Beaupre | |
| 2006/0129140 A1 | 6/2006 | Todd et al. | |
| 2006/0135975 A1 | 6/2006 | Perkins | |
| 2006/0145540 A1 | 7/2006 | Mezhinsky | |
| 2006/0189948 A1 | 8/2006 | Boukhny et al. | |
| 2006/0190003 A1 * | 8/2006 | Boukhny et al. | 606/107 |
| 2006/0211943 A1 | 9/2006 | Beaupre | |
| 2006/0217672 A1 | 9/2006 | Chon | |
| 2006/0217739 A1 | 9/2006 | Tjia et al. | |
| 2006/0264970 A1 | 11/2006 | Ernest et al. | |
| 2007/0016236 A1 | 1/2007 | Beaupre | |
| 2007/0060926 A1 | 3/2007 | Escaf | |
| 2007/0073325 A1 | 3/2007 | Stulen et al. | |
| 2007/0129723 A1 | 6/2007 | Houser et al. | |
| 2007/0191713 A1 | 8/2007 | Eichmann et al. | |
| 2007/0239025 A1 | 10/2007 | Wiener et al. | |
| 2007/0255196 A1 | 11/2007 | Wuchinich | |
| 2007/0260173 A1 | 11/2007 | Boukhny et al. | |
| 2007/0260200 A1 | 11/2007 | Boukhny | |
| 2008/0051814 A1 | 2/2008 | Beaupre | |
| 2008/0058708 A1 | 3/2008 | Akahoshi | |
| 2008/0103418 A1 | 5/2008 | Wuchinich | |
| 2008/0139994 A1 | 6/2008 | Mackool et al. | |
| 2008/0200940 A1 | 8/2008 | Eichmann et al. | |
| 2008/0234710 A1 | 9/2008 | Neurohr et al. | |
| 2008/0281253 A1 | 11/2008 | Injev et al. | |
| 2008/0294087 A1 | 11/2008 | Steen et al. | |
| 2008/0300611 A1 | 12/2008 | Houser et al. | |
| 2009/0005712 A1 | 1/2009 | Raney | |
| 2009/0030311 A1 | 1/2009 | Stulen et al. | |
| 2009/0030437 A1 | 1/2009 | Houser et al. | |
| 2009/0030439 A1 | 1/2009 | Stulen | |
| 2009/0036911 A1 | 2/2009 | Stulen | |
| 2009/0036913 A1 | 2/2009 | Wiener et al. | |
| 2009/0036914 A1 | 2/2009 | Houser | |
| 2009/0066192 A1 | 3/2009 | Taki et al. | |
| 2009/0093750 A1 | 4/2009 | Herman | |
| 2009/0131885 A1 | 5/2009 | Akahoshi | |
| 2009/0131962 A2 | 5/2009 | Houser et al. | |
| 2009/0143795 A1 | 6/2009 | Robertson | |
| 2009/0143806 A1 | 6/2009 | Witt et al. | |
| 2009/0264909 A1 | 10/2009 | Beaupre | |
| 2009/0264910 A1 | 10/2009 | Laufer | |
| 2009/0270891 A1 | 10/2009 | Beaupre | |
| 2010/0004585 A1 | 1/2010 | Boukhny et al. | |
| 2010/0004586 A1 | 1/2010 | Boukhny | |
| 2010/0010419 A1 | 1/2010 | Akahoshi | |
| 2010/0036256 A1 | 2/2010 | Boukhny et al. | |
| 2010/0042126 A1 | 2/2010 | Houser et al. | |
| 2010/0057118 A1 | 3/2010 | Dietz et al. | |
| 2010/0063525 A1 | 3/2010 | Beaupre et al. | |
| 2010/0063526 A1 | 3/2010 | Beaupre et al. | |
| 2010/0063527 A1 | 3/2010 | Beaupre et al. | |
| 2010/0063528 A1 | 3/2010 | Beaupre | |
| 2010/0069825 A1 | 3/2010 | Raney | |
| 2010/0069828 A1 | 3/2010 | Steen et al. | |
| 2010/0087758 A1 | 4/2010 | Beaupre et al. | |
| 2010/0087846 A1 | 4/2010 | Dimalanta | |
| 2010/0094321 A1 | 4/2010 | Akahoshi et al. | |
| 2010/0106173 A1 | 4/2010 | Yoshimine | |
| 2010/0262172 A1 | 10/2010 | Houser et al. | |
| 2010/0324581 A1 | 12/2010 | Mackool et al. | |
| 2010/0331743 A1 | 12/2010 | Rabiner et al. | |
| 2010/0331869 A1 | 12/2010 | Voegele et al. | |
| 2010/0331870 A1 | 12/2010 | Wan et al. | |
| 2010/0331871 A1 | 12/2010 | Nield et al. | |
| 2010/0331872 A1 | 12/2010 | Houser et al. | |
| 2011/0004149 A1 | 1/2011 | Artsyukhovich et al. | |
| 2011/0009374 A1 | 1/2011 | Keller | |
| 2011/0015561 A1 | 1/2011 | Akahoshi | |
| 2011/0015658 A1 | 1/2011 | Vijfvinkel | |
| 2011/0082486 A1 | 4/2011 | Messerly et al. | |
| 2011/0087212 A1 | 4/2011 | Aldridge et al. | |
| 2011/0087213 A1 | 4/2011 | Messerly et al. | |
| 2011/0087214 A1 | 4/2011 | Giordano et al. | |
| 2011/0087215 A1 | 4/2011 | Aldridge et al. | |
| 2011/0087217 A1 | 4/2011 | Yates et al. | |
| 2011/0087256 A1 | 4/2011 | Wiener et al. | |
| 2011/0166502 A1 | 7/2011 | Nallakrishnan | |
| 2011/0172588 A1 | 7/2011 | Akahoshi | |
| 2011/0196287 A1 | 8/2011 | Robertson et al. | |
| 2011/0196403 A1 | 8/2011 | Robertson et al. | |
| 2011/0196404 A1 | 8/2011 | Dietz et al. | |
| 2011/0288452 A1 | 11/2011 | Houser et al. | |
| 2011/0319918 A1 | 12/2011 | Beaupre | |
| 2012/0010537 A1 | 1/2012 | Young et al. | |
| 2012/0029546 A1 | 2/2012 | Robertson | |
| 2012/0072197 A1 | 3/2012 | Ovchinnikov | |
| 2012/0078139 A1 | 3/2012 | Aldridge et al. | |
| 2012/0123458 A1 | 5/2012 | Giordano et al. | |
| 2012/0197215 A1 | 8/2012 | Akahoshi | |
| 2012/0323265 A1 | 12/2012 | Stulen | |
| 2012/0330338 A1 | 12/2012 | Messerly | |
| 2013/0035706 A1 | 2/2013 | Giordano et al. | |
| 2013/0035707 A1 | 2/2013 | Giordano et al. | |

FOREIGN PATENT DOCUMENTS

| | | |
|---|---|---|
| CA | 2098403 A1 | 6/1992 |
| DE | 203229 C | 10/1908 |
| DE | 203229 B3 | 10/1983 |
| DE | 3624243 A1 | 1/1988 |
| DE | 8816114 U1 | 2/1989 |
| DE | 4012882 A1 | 10/1991 |
| DE | 10146011 A1 | 4/2003 |
| EP | 0250914 A2 | 1/1988 |
| EP | 0359217 A2 | 3/1990 |
| EP | 0456470 A1 | 11/1991 |
| EP | 0482847 A1 | 4/1992 |
| EP | 0514810 A1 | 5/1992 |
| EP | 0674350 A1 | 9/1995 |
| EP | 0830845 A1 | 3/1998 |

(56) References Cited

FOREIGN PATENT DOCUMENTS

| | | |
|---|---|---|
| EP | 0968684 A1 | 1/2000 |
| EP | 970659 A1 | 1/2000 |
| EP | 970660 A1 | 1/2000 |
| EP | 0830845 B1 | 8/2003 |
| EP | 1693027 A1 | 8/2006 |
| EP | 970659 B1 | 10/2006 |
| EP | 970660 B1 | 10/2006 |
| EP | 0968684 B1 | 12/2006 |
| EP | 1852096 A1 | 11/2007 |
| EP | 1693027 B1 | 7/2008 |
| EP | 1990032 A1 | 11/2008 |
| EP | 2322106 A2 | 5/2011 |
| EP | 2322106 A3 | 3/2012 |
| ES | 2116203 A1 | 7/1998 |
| ES | 2116203 B1 | 2/1999 |
| FR | 2641693 | 7/1990 |
| FR | 2707872 A1 | 1/1995 |
| GB | 1457530 A | 12/1976 |
| GB | 2247174 A | 2/1992 |
| GB | 2365775 A | 2/2002 |
| GB | 2374290 A | 10/2002 |
| JP | S59-24013 | 2/1984 |
| JP | 62136398 A | 6/1987 |
| JP | 62-207450 A | 9/1987 |
| JP | 63111115 U | 7/1988 |
| JP | 63305856 A | 12/1988 |
| JP | 01027549 A | 1/1989 |
| JP | 02123216 U | 10/1990 |
| JP | 03021232 A | 1/1991 |
| JP | U H05 62225 | 8/1993 |
| JP | 7110277 B | 11/1995 |
| JP | H09-313496 | 12/1997 |
| JP | 2000-070279 A | 3/2000 |
| JP | 2001-061847 | 3/2001 |
| JP | 2001-104326 | 4/2001 |
| JP | 2001178736 A | 7/2001 |
| JP | 2003033364 A | 2/2003 |
| JP | 2003116870 A | 4/2003 |
| JP | 2006-223865 | 8/2006 |
| JP | 2009009656 A | 1/2009 |
| NL | 2001401 C2 | 9/2009 |
| SU | 1000028 | 2/1983 |
| SU | 1026793 | 7/1983 |
| SU | 1695900 A1 | 12/1991 |
| WO | 86/02257 A1 | 4/1986 |
| WO | 87/05793 A1 | 10/1987 |
| WO | 92/07622 A1 | 5/1992 |
| WO | 93/14709 A1 | 8/1993 |
| WO | 94/08518 A1 | 4/1994 |
| WO | 95/10233 A1 | 4/1995 |
| WO | 95/20374 A1 | 8/1995 |
| WO | 96/35923 A2 | 11/1996 |
| WO | 96/35923 A3 | 3/1997 |
| WO | 98/23212 A1 | 6/1998 |
| WO | 98/35721 A2 | 8/1998 |
| WO | 98/35721 A3 | 10/1998 |
| WO | 99/18901 A1 | 4/1999 |
| WO | 99/35982 A1 | 7/1999 |
| WO | 99/45868 A1 | 9/1999 |
| WO | 00/48520 A1 | 8/2000 |
| WO | 01/24744 A1 | 4/2001 |
| WO | 01/41672 A2 | 6/2001 |
| WO | 01/52782 A1 | 7/2001 |
| WO | 01/41672 A3 | 12/2001 |
| WO | 01/97728 A1 | 12/2001 |
| WO | 02/17833 A1 | 3/2002 |
| WO | 02/26016 A2 | 4/2002 |
| WO | 02/056806 A1 | 7/2002 |
| WO | 02/083010 A1 | 10/2002 |
| WO | 03/043550 A1 | 5/2003 |
| WO | 03/095028 A1 | 11/2003 |
| WO | 2004/080505 A2 | 9/2004 |
| WO | 2004/080505 A3 | 7/2005 |
| WO | 2005/084552 A1 | 9/2005 |
| WO | 2005/084553 A1 | 9/2005 |
| WO | 2005/092022 A2 | 10/2005 |
| WO | 2005/092023 A2 | 10/2005 |
| WO | 2007/119107 A2 | 10/2007 |
| WO | 2007/119107 A3 | 12/2007 |
| WO | 2008/017909 A1 | 2/2008 |
| WO | 2008/065323 A1 | 6/2008 |
| WO | 2009/120075 A1 | 10/2009 |
| WO | 2010/089629 A2 | 8/2010 |
| WO | 2010/093347 A1 | 8/2010 |
| WO | 2011/002576 A1 | 1/2011 |
| WO | 2012/036795 A2 | 3/2012 |
| WO | 2012/036795 A3 | 7/2012 |

OTHER PUBLICATIONS

Sandor, Bela I., et al., Mechanics of Solids, 1999, 9 pages, CRC Press, LLC.

Adams, Maurice L., Jr., Rotating Machinery Vibration, From Analysis to Troubleshooting, book, © 2001, 29 pages, Marcel Dekker, Inc., New York, NY.

Alterman, Z., et al., Propagation of Elastic Waves in a Semi-Infinite Cylindrical Rod Using Finite Difference Methods, J. Sound Vib., 1970, pp. 115-145, vol. 13 (2).

Astashev, V.K., et al., "Ultrasonic cutting as a nonlinear (vibro-impact) process," Ultrasonics, vol. 36 (1998), pp. 89-96.

Bert, C.W., et al., Whirling of Composite-Material Driveshafts including Bending-Twisting Coupling and Transverse Shear Deformation, Journal of Vibration and Acoustics, Jan. 1995, pp. 17-21, vol. 117.

Bhaskar, Atula, Waveguide modes in elastic rods, Mathmatical, Physical & Engineering Sciences, Nov. 14, 2002, pp. 175-194, vol. 459, Royal Society Publishing, UK.

Bishop, R.E.D., et al., On Coupled Bending and Torsional Vibration of Uniform Beams, Journal of Sound and Vibration, 1989, vol. 131(3), pp. 457-464, Brunel University, Uxbridge, England.

Cascante, Giovanni, et al., Flexural excitation in a standard torsional-resonant column device, Can Geotech. J., 1998, pp. 478-490, vol. 35, NRC Canada.

Cheng, J.K., et al., Stability and Nonlinear Dynamics of a Horizontally Base-Excited Rigid Rod with Unsymmetric End Stiffnesses, Journal of Vibration and Acoustics, Jan. 1993, pp. 85-95, vol. 115.

Cohen, R., et al., Coupled Torsional and Transverse Vibration of Unbalanced Rotor, Journal of Applied Mechanics, Sep. 1985, pp. 701-705, vol. 52.

Designer.K, et al., A New Application System for Laser and Ultrasonic Therapy in Endoscopic Surgery, SPIE, 1996, pp. 268-274, vol. 2922.

Dimalanta, Ramon C., "Extended Point Phacoemulsification Tip," U.S. Appl. No. 12/616,537, filed Nov. 11, 2009, 27 pages. (3623).

Dokumaci. E, an Exact Solution for Coupled Bending and Torsion Vibrations of Uniform Beams Having Single Cross-Sectional Symmetry, Journal of Sound and Vibration, 1987, pp. 443-449, vol. 119(3), Academic Press Limited.

Dunn, D.J., Solid Mechanics Dynamics Tutorial—forced Vibrations, downloaded from http://web.archive.org/web/20070906003853/http://www.freestudy.co.us/dynamics/, archive dated Sep. 6, 2007, filed dated May 4, 2007, pp. 1-18.

Eastwood, David C., Office Action, U.S. Appl. No. 11/232,205, Feb. 27, 2009, 5 pages.

Eastwood, David C., Office Action, U.S. Appl. No. 11/232,205, Jun. 23, 2009, 7 pages.

Eastwood, David C., Office Action, U.S. Appl. No. 11/232,205, Oct. 19, 2009, 6 pages.

Etneir, Shelley A., Twisting and Bending of Biological Beams: Distribution of Biological Beams in a Stiffness Mechanospace, Biol. Bull., Aug. 2003, pp. 36-46, vol. 205, Marine Biological Laboratory, Durham, North Carolina.

Friend, James R., et al., A Novel Torsional Microtransducer Using Bulk PZT, 2002 IEEE Ultrasonics Symposium, pp. 1123-1126, Tokyo Institute of Technology, Yokohama, Japan.

Golyamina, I.P., et al., Ultrasonic Vibratory Systems with a Curved Working Section, Sov. Phys. Acoust., Mar.-Apr. 1990, pp. 135-138, vol. 36(2), American Institute of Physics.

(56) References Cited

OTHER PUBLICATIONS

Graff, K.F., "Process Applications of Power Ultrasonics—A Review," IEEE Ultrasonics Symposium Proceedings, Cat. #74, CH)896-ISU, 1974.

Gregory, R.D., et al., Axisymmetric Waves in a Semi-Infinite Elastic Rod, Q.JI Mech. App. Math., pp. 327-337, vol. 42, Pt. 2, Oxford University Press 1989.

Haeggstrom, Edward, et al., Capacitive Micromachined Ultrasonic Transducer Based Integrated Actuator for Atomic Force Microscope Cantilevers, IEEE-NANO, Aug. 26, 2002, pp. 45-49.

Ilanko, S., Whirling Speed of Shafts, 2005, pp. 64-65.

International Searching Authority, International Search Report, International Application No. PCT/US2011/046362, Mar. 16, 2012, 4 pages.

International Searching Authority, Written Opinion of the International Searching Authority, International Application No. PCT/US10/37610, Sep. 16, 2010, 7 pages.

International Searching Authority, Written Opinion of the International Searching Authority, International Application No. PCT/US2011/046362, Mar. 16, 2012, 5 pages.

Kim, Yong Y., Flexural-Torsional Coupled Vibration of Rotating Beams Using Orthogonal Polynomials, Thesis submitted to the Faculty of the Virginia Polytechnic Institute and State University, May 1, 2000, 117 pages, Blacksburg, Virginia.

Kuwahara, Yasuharu, Aspiration Method of a Hard Cataract, book, 1972, pp. 1-15, 31-75 and 96-115, Igaku Shoin Ltd., Tokyo, Japan.

Allen, Henry F. reviewing Aspiration Method of a Hard Cataract: Ultrasonic Vibration by Yasuharu Kuwahara, Arch Ophthalmol., Sep. 1973, p. 260, vol. 90.

Kuwahara, Yasuharu, Aspiration Method of Senile Cataract, Keio J. Med., Jun. 18, 1970, pp. 115-133, vol. 19, Tokyo, Japan.

Kuwahara, Yasuharu, Aspiration Method of Senile Cataract, Keio J. Med., May-Jun. 1971, pp. 97-107, vol. 2, No. 3, Tokyo, Japan.

Lee, Jaehong, et al., Flexural-torsional behavior of thin-walled composite beams, Thin Walled Structures, 2004, pp. 1293-1305, vol. 42, Elsevier Ltd., South Korea.

Love, A.E.H., A Treatise on the Mathematical Theory of Elasticity, 1920, Third Edition, pp. i-vi, 281-296, 315-333, and 387-460.

Mao, Cheng, et al., Coupled Torsional-Flexural Vibration of Shaft Systems in Mechanical Engineering-II. FE-TM Impedance Coupling Method, Computers and Structures, 1996, pp. 845-849, vol. 58, No. 4, Elsevier Science, Ltd., Great Britain.

Markov, A.L., "The Calculation and Design of Vibrators for Ultrasonic Machining," Soviet Progress in Apppplied Ultrasonics, vol. 1—Ultrasound in Industrial Processing and Control; Edited by V.F. Nozdreva Authorized translation from the Russian; Consultants Bureau, New York, 1964.

Mitaku, Shigeki, et al., Composite torsional quartz transducer for shear ultrasonic measurements of aqueous liquids, Rev. Sci. Instrum., 1979, pp. 1437-1440, vol. 50, No. 11, American Institute of Physics.

Nicholson, N.C., et al., Mode propagation of ultrasound in holow waveguides, Ultrasonics, 1991, pp. 411-416, vol. 29.

Obazawa, Studies on the Influence of Various Untrasonic Characters on Phacoemulsification Effects, Aug. 10, 1969, pp. 135-153, 73(8).

Oliver, Jack, Elastic Wave Dispersion in a Cylindrical Rod by a Wide-Band Short-Duration Pulse Technique*, The Journal of the Acoustical Society of America, Feb. 1957, pp. 189-194, vol. 29, No. 2.

Onaran, A. Guclu, et al., Tapping mode and elasticity imaging in liquids using an atomic force microscope actuated by acoustic radiation pressure, Applied Physics Letters, May 27, 2002, pp. 4063-4065, vol. 80, No. 21, American Institute of Physics.

Phillips, J.W., et al., On the Theory of Pulse Propagation in Curved Beams, Journal of Sound and Vibration, 1972, pp. 247-258, vol. 24(2).

Plaut, R.H., et al., Parametric, External and Comvination Resonances in Coupled Flexural and Torsional Oscillations of an Unbalanced Rotating Shaft, Journal of Sound and Vibration, 1995, pp. 889-897, vol. 183(5).

Qin, Qing Hua, et al., Coupled Torsional-Flexural Vibration of Shaft Systems in Mechanical Engineering-I. Finite Element Model, Computers and Structures, 1996, pp. 835-843, vol. 58, No. 4, Elsevier Science Ltd., Great Britain.

Rabe, U., et al., Vibrations of free and surfacecoupled atomic force microscope cantilevers: Theory and experiment, Review of Scientific Instruments, 1996, pp. 3281-3293 vol. 67, No. 9, American Institute of Physics.

Rees, David W., Mechanics of Solids and Structures, Chapter 5: Theories of Torsion, 2000, pp. 197-252.

Rossing, Thomas D., et al., Laboratory observation of elastic waves in solids, Am. J. Phys., Dec. 1990, pp. 1153-1162, vol. 58, No. 12.

Russell, Daniel A., Vibrational Behavior of a Hockey Stick, © 2004-2011, 3 pages.

Satonobu, et al., Traveling Wave Excitation in a Flexural Vibration Ring by Using a Torsional-Flexural Composite Tranducer, IEEE Transactions on Ultrasonics, Ferroelectrics, and Frequency Control, Jul. 2001, pp. 1054-1059, vol. 48, No. 4.

Sazonov, I.A., Features of the Vibration of Curved Sectional Roads in Ultrasonic Oscillating Systems, Acoustics Institute, Moscow, Jun. 1989, pp. 62-68, vol. 25, No. 6, Plenum Publishing Corporation.

Sazonov, I.A., Selection of the centroidal line in curved beams of variable cross section, Sov. Phys. Acoust., 1990, pp. 298-301, vol. 36(3).

Sazonov, I.A., Wave propagation in curved rods of variable cross section, Sov. Phys. Acoust., Mar.-Apr. 1977, pp. 163-167, vol. 23, No. 2.

Selektor, LY .. et al. "Separation of undamaged single nerve fibers by using an ultrasonic microscalpel," Biull Eksp Biol Med. Dec. 1985; 100(12), pp. 761-762—A blade of microscalpel made of sewing needle connected to waveguide through the steel plate. Such construction is developed to decrease vertical fluctations of blade.

Severson, Ryan J., Office Action, U.S. Appl. No. 11/060,827, Aug. 17, 2009, 8 pages.

Severson, Ryan J., Office Action, U.S. Appl. No. 11/060,827, Jun. 27, 2007, 6 pages.

Severson, Ryan J., Office Action, U.S. Appl. No. 11/060,827, Mar. 11, 2008, 6 pages.

Severson, Ryan J., Office Action, U.S. Appl. No. 11/060,827, Mar. 20, 2007, 8 pages.

Severson, Ryan J., Office Action, U.S. Appl. No. 11/060,827, May 11, 2009, 11 pages.

Severson, Ryan J., Office Action, U.S. Appl. No. 11/060,827, May 30, 2007, 6 pages.

Severson, Ryan J., Office Communication, U.S. Appl. No. 11/060,827, May 30, 2008, 6 pages.

Severson, Ryan J., Office Action, U.S. Appl. No. 11/060,827, Nov. 10, 2008, 7 pages.

Severson, Ryan J., Office Action, U.S. Appl. No. 11/060,827, Sep. 19, 2007, 9 pages.

Shuyu, Lin, Sandwiched Piezoelectric Ultrasonic Transducers of Longitudinal-Torsional Compound Vibrational Modes, IEEE Transactions of Ultrasonics, Ferroelectrics, and Frequency Control, Nov. 1997, pp. 1189-1197, vol. 44, No. 6.

Shuyu, Lin, Study on the prestressed sandwich piezoelectric ceramic ultrasonic transducer of torsional-flexural composite vibrational mode, J. Acoust. Soc. Am., Aug. 2002, pp. 511-517, vol. 112, No. 2.

Smith, W.M.R., et al., "Factors in the design of ultrasonic probes," Ultrasonics, vol. 17, Issue 1, Jan. 1979, pp. 20-26.

Steinert, Roger F., Cataract Surgery, Chapter 17: Phaco Chop, 2010, pp. 205-213, Third Edition, Elsevier.

Steinert, Roger F., et al., Cataract Surgery, Chapter 7: The Phaco Machine: The Physical Principles Guiding its Operation, 2010, pp. 75-92, Third Edition, Elsevier.

Stumpff, U., "Die Ereugung and Ubertragung von Ultraschalldehnwellen hoher Energiedichten in flexiblen Wellenleitern im 20 kHz-Bereich fur therapeutische Anwendungen: The generation and transmission of high energy densities in ultrasonic quasilongitudinal waves via flexible fibers in the 20 kHz range

(56) References Cited

OTHER PUBLICATIONS for therapeutic applications" Format 136 S. Hochschulschrift Aachen, Techn. Hochsch., Fak. für Elektrotechnik, Sachgruppe(n) 20a Technik, Industrie, Diss., 1978. Comments—p. 33. Abb. (Fig.) 12.

Thoe, T.B., et al., "Review of Ultrasonic Machining," Int. J. Mach. Tools Manufact., vol. 38, No. 4, pp. 239-255, 1998.

Togawa, et al., Application of Ultrasonic Instruments to Physiological Experiments, pp. 43-46, 1992.

Tso, W.K., On the Motion of a Curved and Twisted Rod, Acta Mechanica, 1972, pp. 163-178, vol. 13, Springer-Verlal.

Tsujino, J., et al., Transverse and torsional complex vibration systems for ultrasonic seam welding of metal plates, Ultrasonics, 2000, pp. 67-71, vol. 38, Elsevier Science B.V.

Tsujino, Jiromaru, Ultrasonic Motor Using a One-Dimensional Longitudinal-Torsional Vibration Converter with Diagonal Slits, Smart Mater. Struct. 7, 1998, pp. 345-351.

Vandiver, Kim J., et al., Case Studies of the Bending Vibration and Whirling Motion of Drill Collars, SPE Drilling Engineering, Dec. 1990, pp. 282-290, vol. 5, No. 4, Society of Petroleum Engineers.

Zhou, Guangping, et al., The complex-mode vibration of ultrasonic vibration systems, Ultrasonics, 2002, pp. 907-911, vol. 40, Elsevier Science B.V.

* cited by examiner

Tip material on one side of extended centerline

PHACOEMULSIFICATION HOOK TIP

This application is a continuation of U.S. application Ser. No. 12/496,220, filed Jul. 1, 2009, which is hereby incorporated by reference in its entirety as though fully and completely set forth herein.

FIELD OF THE INVENTION

The present invention generally pertains to phacoemulsification. More particularly, but not by way of limitation, the present invention pertains to phacoemulsification cutting tips.

DESCRIPTION OF THE RELATED ART

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an intraocular lens (IOL).

Cataractous lenses may be removed by a surgical technique called phacoemulsification. During this procedure, a thin phacoemulsification cutting tip may be inserted into the diseased lens and vibrated ultrasonically. The vibrating cutting tip may liquefy or emulsify the lens so that the lens may be aspirated out of the eye. The diseased lens, once removed, may be replaced by an artificial lens.

SUMMARY OF THE INVENTION

In various embodiments, a phacoemulsification tip with a straight shaft and an angled portion off of the straight shaft may include a hook on the angled portion to move an axis of rotation of the tip closer to alignment with a centerline of the shaft. The tip may be configured to torsionally rotate back and forth on an axis perpendicular to a centerline of the shaft (e.g., rotation around a y-axis). In some embodiments, lateral vibrations (e.g., side to side along an x-axis or z-axis perpendicular to the y-axis) that result from torsional rotation around the y-axis in a tip without the hook may be reduced through use of the hook to balance the otherwise eccentrically weighted hook.

BRIEF DESCRIPTION OF THE DRAWINGS

For a more complete understanding of the present invention, reference is made to the following description taken in conjunction with the accompanying drawings in which.

It is to be understood that both the foregoing general description and the following detailed description are exemplary and explanatory only and are intended to provide a further explanation of the present invention as claimed.

DETAILED DESCRIPTION OF THE EMBODIMENTS

Figure 1A:
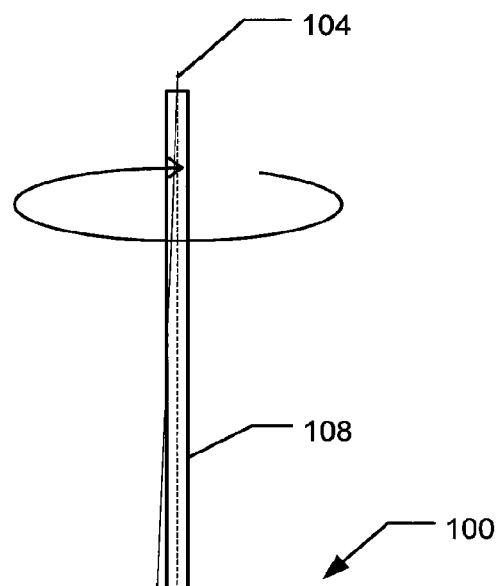
FIGS. 1a-b illustrate a phacoemulsification tip with a distal end that is angled relative to centerline of the tip shaft.
Figure 1B:
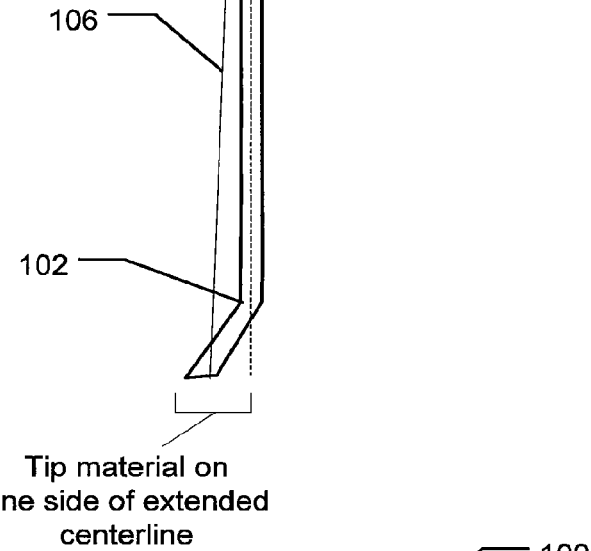
Figure 1B:
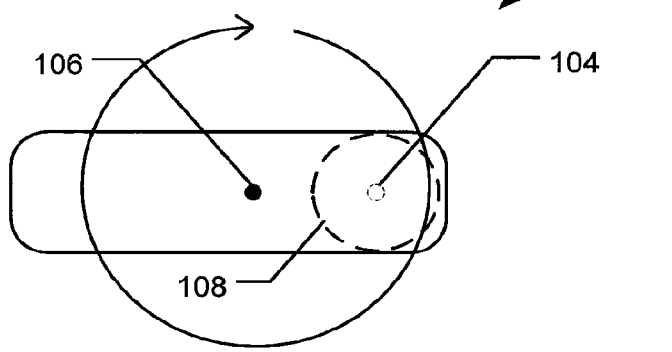

FIGS. 1a-b illustrate a phacoemulsification cutting tip 100 with a distal end that is angled relative to a tip shaft 108. The cutting tip 100 may include a predominantly straight shaft 108 with the far distal portion bent on an angle 102 (e.g., approximately a 20 degree bend). Other angles are also contemplated (e.g., 5 degree bend, 35 degree bend, etc). The distal portion may have a flared and/or beveled distal end. The cutting tip 100 may be used in conjunction with a phacoemulsification handpiece 204 (e.g., see FIG. 2). When used with the handpiece 204, the cutting tip 100 may use longitudinal movement and/or transverse movement. Cutting tip 100 may be eccentrically weighted with tip material on only one side of the extended shaft centerline 104 (because of angle 102). As used herein "extended shaft centerline" refers to a line that includes and is collinear with the shaft centerline (as illustrated in, for example, FIGS. 1a and 3a). The eccentrically weighted cutting tip may therefore have a center of rotation 106 that is displaced from the extended shaft centerline 104 of the shaft 108 through at least a portion of the cutting tip 100 (e.g., at least along the bottom 10% of the length of the cutting tip 100). Other portions of the length are also contemplated (e.g., the center of rotation 106 may be displaced from the extended shaft centerline 104 through 50% of the length or gradually over the entire length of the cutting tip 100). For example, as seen in FIG. 3a, the center of rotation 106 may follow an angle of approximately 0 to 10 degrees off parallel with the extended shaft centerline 104. Other angles and configurations of the center of rotation 106 are also contemplated (e.g., the center of rotation 106 may be displaced from and parallel to the extended shaft centerline 104). Rotating the eccentrically weighted tip and/or the resistance of fluid against the moving cutting tip 100 may cause lateral vibrations in the eccentrically weighted cutting tip 100 when the cutting tip 100 is vibrated (e.g., rotationally and/or longitudinally) through the shaft 108.

Figure 2A:
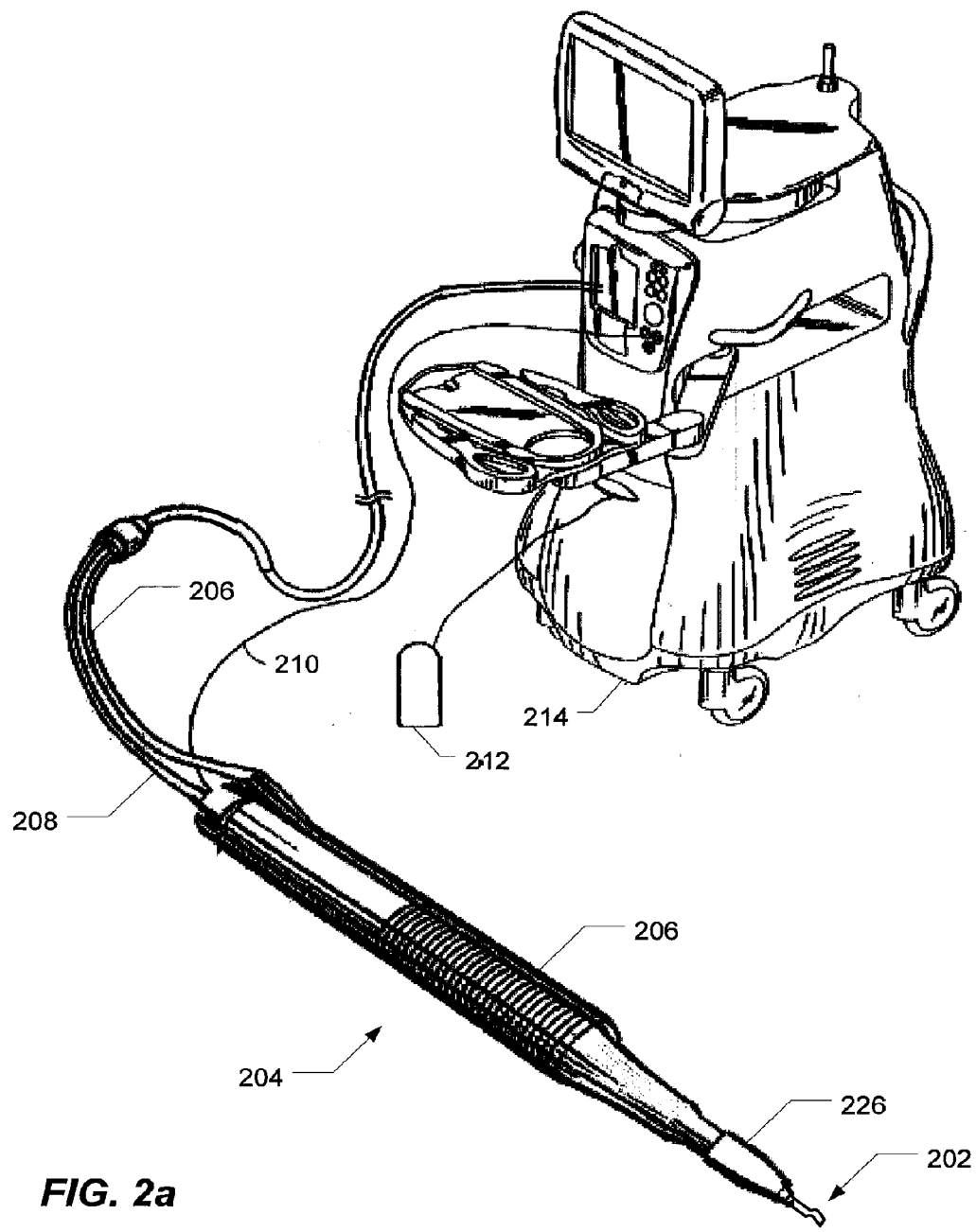
FIG. 2a illustrates a phacoemulsification surgical console connected to a handpiece through an irrigation line and an aspiration line, according to an embodiment.
Figure 3A:
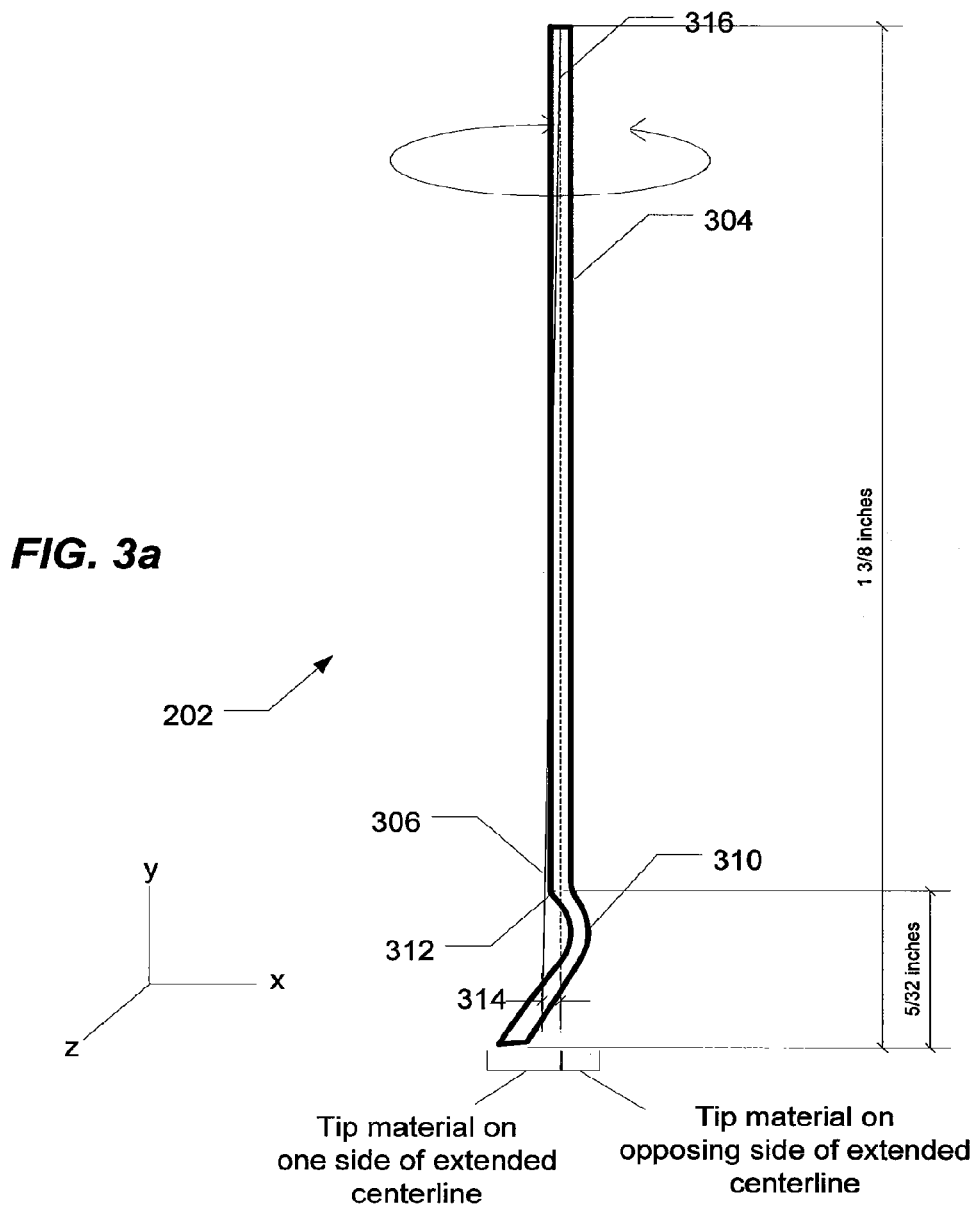
FIGS. 3a-b illustrate an embodiment of the hooked tip.
Figure 3B:
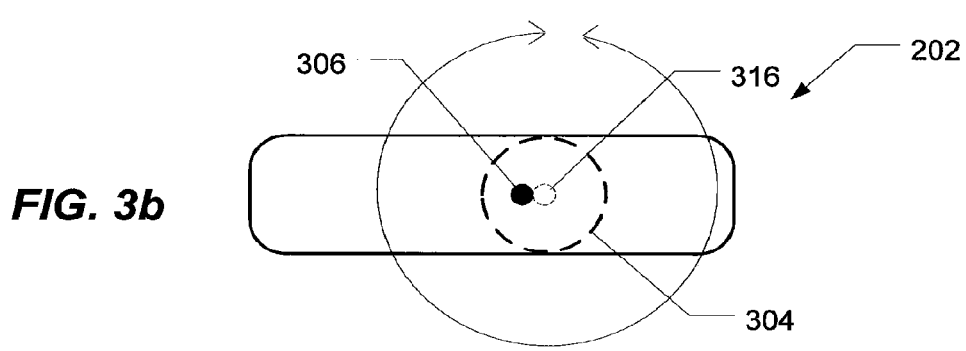

FIG. 2a illustrates a phacoemulsification surgical console 214 connected to a handpiece 204 through an irrigation line 206 and an aspiration line 208. In some embodiments, power may be supplied to handpiece 204 through electrical cable 210 and flow through lines 206 and 208 may be controlled by a user (e.g., via footswitch 212) to perform a phacoemulsification procedure. One example of a handpiece for a phacoemulsification procedure is described in U.S. Patent Application Publication entitled "Ultrasound Handpiece," Publication No. 2006/0041220, Ser. No. 11/183,591, by Mikhail Boukhny, James Y. Chon, and Ahmad Salehi filed Jul. 18, 2005, which is hereby incorporated by reference in its entirety as though fully and completely set forth herein.

Figure 2B:
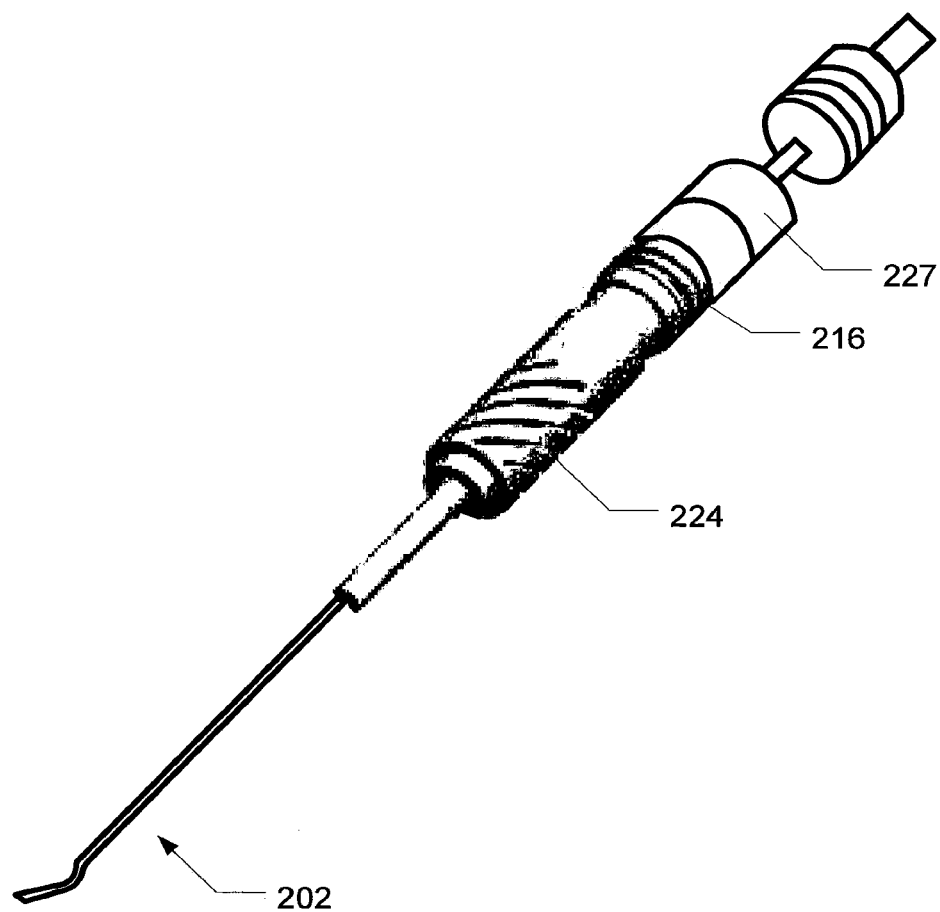
FIG. 2b illustrates an ultrasonic horn attached to the hooked tip, according to an embodiment.

In some embodiments, the handpiece 204 may include at least one set of piezoelectric elements 227 polarized to produce longitudinal motion when excited at a relevant resonant frequency. As seen in FIG. 2b, the piezoelectric crystals 227 may be connected to an ultrasonic horn 216 to which a cutting tip 202 is attached. The horn 216 and/or the cutting tip 202 may include a plurality of diagonal slits or grooves 224. The slits or grooves 224 may produce torsional movement in the cutting tip 202 when the piezoelectric crystals are excited at a resonant frequency. Movement of the cutting tip 202 caused by the grooves 224 engaging fixed elements in the handpiece 204 may include a torsional rotational component relative to an axis of rotation collinear with a centerline of the horn 216.

In some embodiments, handpiece 204 may be coupled to a phacoemulsification cutting tip 202. As seen in FIG. 3a, the phacoemulsification cutting tip 202 may include a hook 310 located near angle 312 in a shaft 304 of the cutting tip 202. In some embodiments, the hook 310 may include a curve, a bump, or an elbow geometry that may act as a counterweight by placing tip material on an opposing side of the extended shaft centerline 316 than tip material angled away from the extended shaft centerline below angle 312. In some embodiments, the cutting tip may have a diameter in a range of approximately 0.5 mm to 2 mm (e.g., 1.5 mm). In some embodiments, the cutting tip may have a flared tip with a diameter at a top of the tip of approximately 1.5 mm and a diameter near a distal end of the tip of 0.5 mm (other diameters and configurations are also contemplated). In one embodiment, the cutting tip 202 may have a length of approximately 1 and ⅜ inches with a hook portion length of approximately 5/32 inches. Other dimensions are also contemplated. Hook 310 may act to move a center of rotation 306 to lie near (e.g., within a distance 314 of 0.25*shaft diameter) or on extended shaft centerline 316. Other distances between the center of rotation 306 and the extended shaft centerline 316 are also contemplated (e.g., within a distance of 0.5*shaft diameter, within a distance equal to the shaft diameter, etc). In some embodiments, motion of a top portion of the cutting tip 100 may be constrained due to its close proximity to the horn gripping the cutting tip 100 such that an axis of rotation of the top of the cutting tip 100 may lie along the extended shaft centerline 316 while a distal end of the cutting tip 100 (e.g., along approximately 10% of the bottom length of the cutting tip 100) may be distanced from the extended shaft centerline 316. In some embodiments, there may be a gradual displacement of the center of rotation 306 relative to the extended shaft centerline 316 from the top of the cutting tip 100 to the bottom of the cutting tip 100. As noted above, the hook 310 may effectively move the center of rotation 306 to lie near (e.g., within a distance 314 of 0.25*shaft diameter) or on extended shaft centerline 316 at the bottom portion of the cutting tip 100.

The hook 310 may include various geometries of varying angle, length or depth of bend, etc. (e.g., see FIGS. 3a and 6a-6c). The geometry of the hook 310 may also be configured to move a line through the center of mass of the tip and parallel to the extended shaft centerline of the cutting tip 202 closer to the extended shaft centerline 316 to reduce eccentric movement (including lateral vibrations) in the cutting tip 202 during rotational and/or longitudinal movements.

In some embodiments, the cutting tip 202 may be ultrasonically torsionally vibrated along a small arc (e.g., +/−5 degrees). The torsional vibrations of cutting tip 202 may result in lateral motions in the shaft 304 and cutting tip 202. The whipping motion may include a side to side torsional motion of the cutting tip 202 perpendicular to the extended shaft centerline 316 (e.g., rotation around the y-axis as seen in FIG. 3a). In some embodiments, lateral vibrations (e.g., side to side along the x-axis or z-axis as seen in FIG. 3a) that result from the eccentrically weighted cutting tip and/or fluid resistance against the back and forth torsional rotation around the y-axis (e.g., cutting tip 100 in FIG. 1a) may be reduced through use of the hook 310 to balance the otherwise eccentrically weighted hook.

Figure 4:
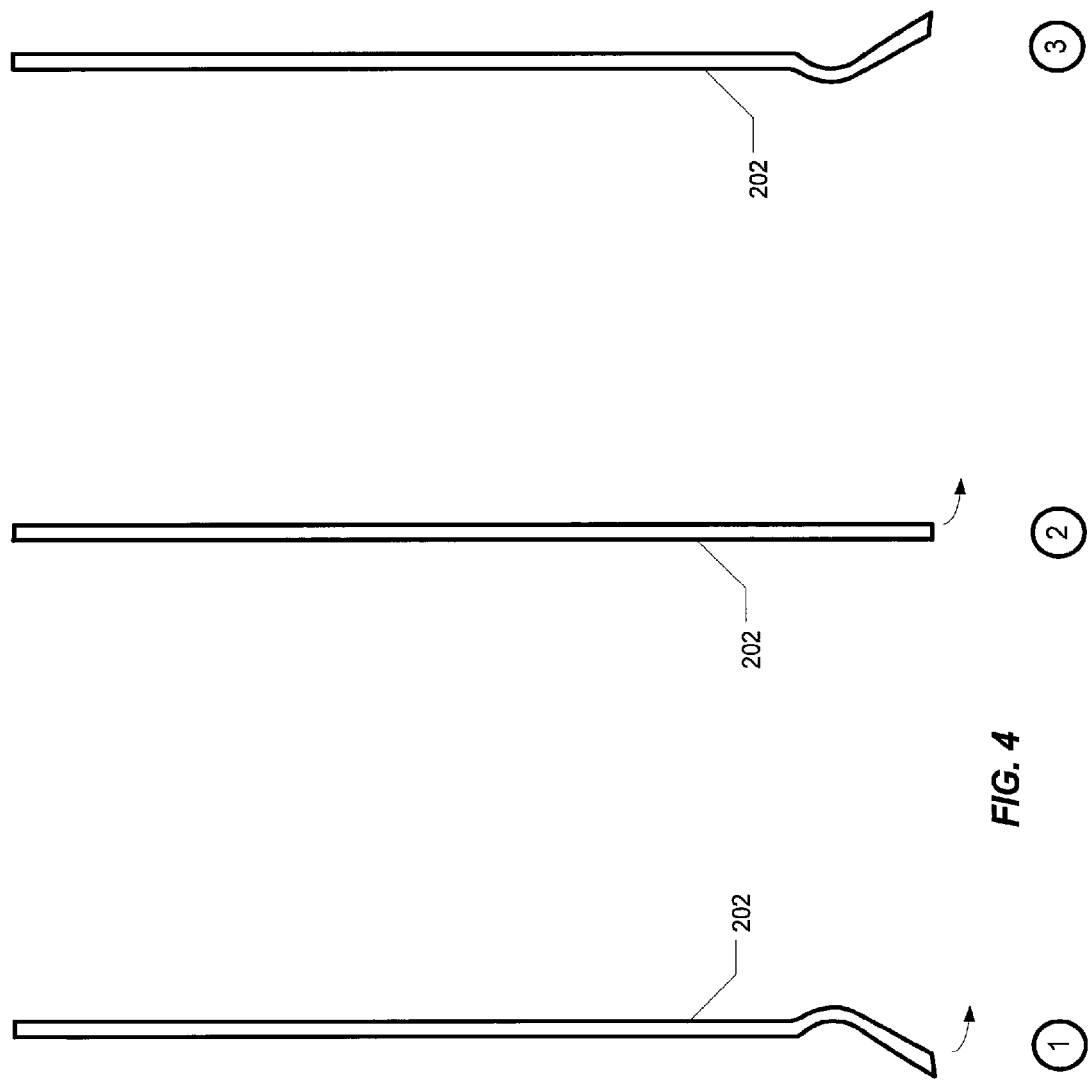
FIG. 4 illustrates motion of the hooked tip, according to an embodiment.

As seen in FIG. 4, in some embodiments, the cutting tip 202 may torsionally rotate back and forth through approximately a 10 degree arc (e.g., plus or minus 5 degrees off center (see middle diagram 2)). In some embodiments, the cutting tip 202 may rotate back and forth at a rate of approximately 31 kHz. Other arcs and rates are also contemplated. For example, an arc of plus or minus 20 degrees and/or a rate of 10-60 kHz may be used. The arc shown in FIG. 4 is exaggerated to show movement (i.e., the total arc shown is 180 degrees, whereas the cutting tip may have limited back and forth rotation on a 10 degree arc).

Figure 5:
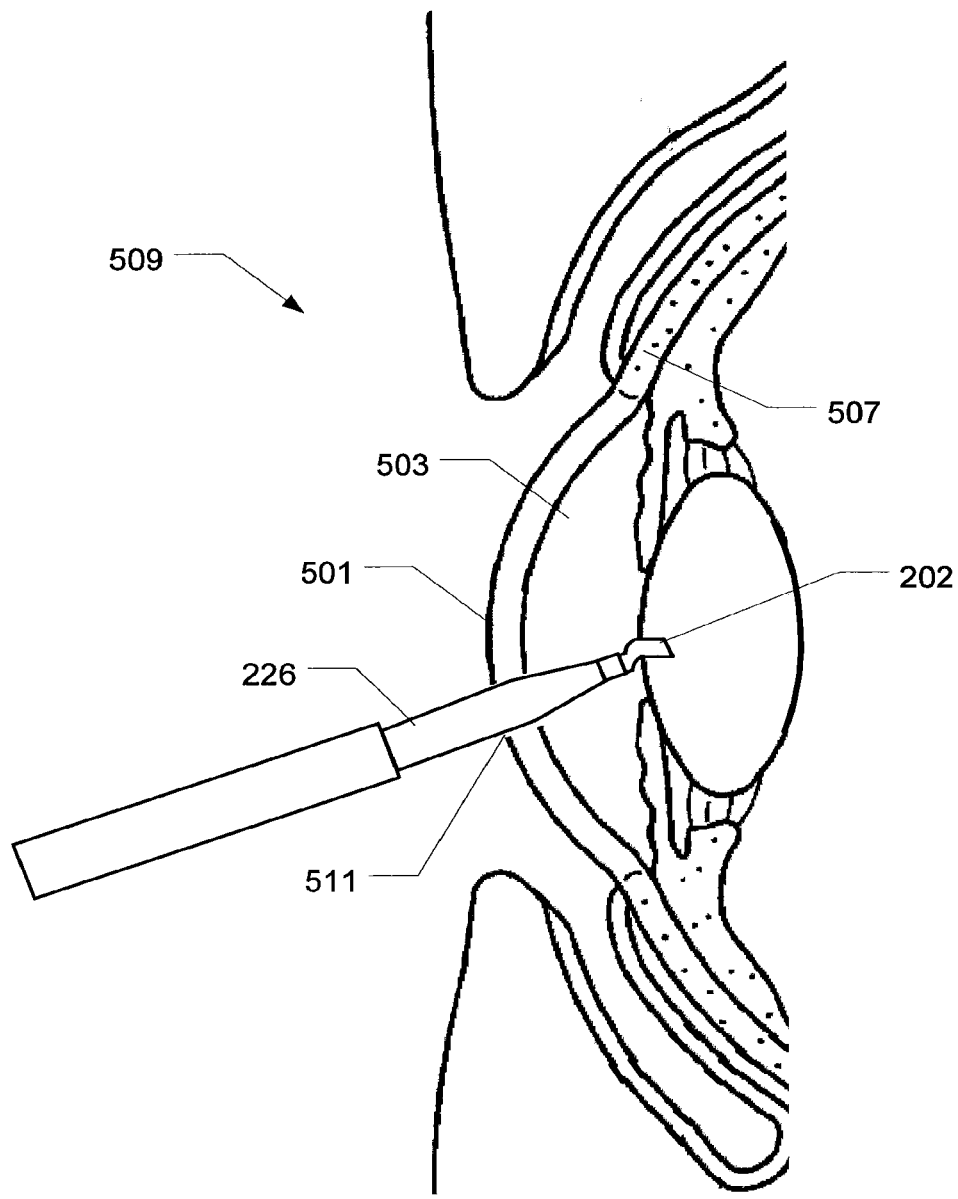
FIG. 5 illustrates a hooked tip inserted into an incision in the eye, according to an embodiment.
Figure 6C:
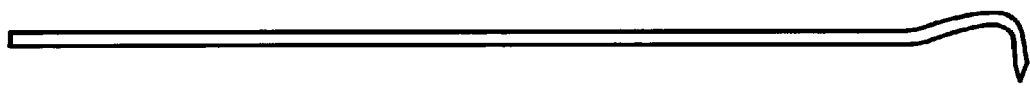
FIGS. 6a-c illustrate additional embodiments of the hooked tip.
Figure 6B:
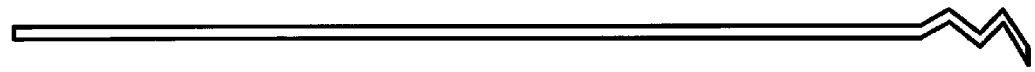
Figure 6A:
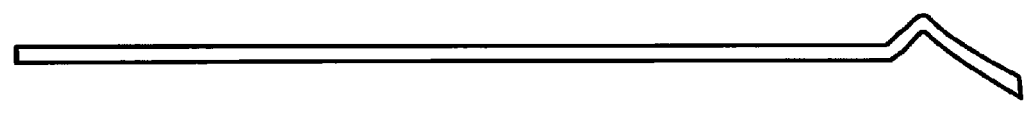

As seen in FIG. 5, when used to perform phacoemulsification, the ends of the cutting tip 202 and an irrigating sleeve 226 may be inserted into a small incision 511 in the cornea 501, sclera 507, or other location in the eye tissue to gain access to, for example, the anterior chamber 503 of the eye 509. In various embodiments, a portion or all of the cutting tip 202 may be inside the irrigating sleeve 226. The cutting tip 202 may be ultrasonically torsionally vibrated along its longitudinal axis within the irrigating sleeve 226 by a crystal-driven ultrasonic horn 216, thereby emulsifying upon contact the selected tissue in situ. The hollow bore of the cutting tip 202 may communicate with the bore in the horn that in turn may communicate with the aspiration line from the handpiece 204 to the console 214 (e.g., see FIG. 2a). A reduced pressure or vacuum source in the console 214 may draw or aspirate the emulsified tissue from the eye 509 through an open end of the cutting tip 202, the bore of the cutting tip 202, the horn bore, and the aspiration line 208 and into a collection device. The aspiration of emulsified tissue may be aided by a saline flushing solution or irrigant that may be injected into the surgical site through the small annular gap between the inside surface of the irrigating sleeve 226 and an outside surface of the cutting tip 202.

Cutting tip 202 may be made from stainless steel or titanium (other materials may also be used). Cutting tip 202 may have an overall length of between 0.50 inches and 1.50 inches (e.g., 1.20 inches). Other lengths are also contemplated. Cutting tip 202 may be formed using conventional metalworking technology and may be electropolished. Shaft 304 may be generally tubular, with an outside diameter of between 0.005 inches and 0.100 inches and an inside diameter of between 0.001 inches and 0.090 inches (other diameters are also contemplated).

Various modifications may be made to the presented embodiments by a person of ordinary skill in the art. Other embodiments of the present invention will also be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A cutting tip and a phacoemulsification surgical handpiece, comprising:
    a phacoemulsification surgical handpiece comprising a horn configured to torsionally vibrate a cutting tip at a rate of approximately 10 to 60 kHz; and
    a cutting tip comprising:
        a first portion comprising a straight shaft comprising a proximal portion of a cutting tip length secured in the horn of the surgical handpiece, wherein the straight shaft has a shaft centerline,
        a distal portion, comprising:
            a second portion forming an angle with the first portion;
            a third portion forming a hook; and
            a distal end with a beveled end; and an aspiration lumen through at least the first portion, wherein the aspiration lumen has an inner diameter between 0.001 inches and 0.09 inches;

wherein the cutting tip has a diameter in a range of approximately 0.5 mm to 2 mm;

wherein the proximal portion of the cutting tip length is constrained by the horn of the surgical handpiece such that the shaft centerline of the proximal portion is aligned with an axis of rotation of the horn;

wherein the first portion, second portion, third portion and distal end are comprised in a single piece;

wherein the second portion, third portion, and distal end together have an axis of rotation relative to the shaft that is substantially aligned with an extended shaft centerline when the proximal portion of the cutting tip length is torsionally vibrated by the phacoemuslfication surgical handpiece at the rate of approximately 10 to 60 kHz, on an arc with an axis of rotation that is aligned with the shaft centerline at the proximal portion.

2. The cutting tip and phacoemulsification surgical handpiece as recited in claim 1, wherein substantially aligned comprises the axis of rotation, at the distal end of the cutting tip, being offset from the extended shaft centerline by a distance less than 0.25 times a diameter of the shaft.

3. The cutting tip and phacoemulsification surgical handpiece as recited in claim 1, wherein substantially aligned comprises the axis of rotation, at the distal end of the cutting tip, being offset from the extended shaft centerline by a distance less than 0.5 times a diameter of the shaft.

4. The cutting tip and phacoemulsification surgical handpiece as recited in claim 1, wherein a first part of the second portion angle is aligned with the extended shaft centerline and wherein a second part of the second portion angle is directed away from the extended shaft centerline.

5. The cutting tip and phacoemulsification surgical handpiece of claim 1, wherein the horn torsionally vibrates the proximal portion of the cutting tip back and forth through an arc of approximately plus 5 degrees to minus 5 degrees.

6. The cutting tip and phacoemulsification surgical handpiece of claim 1,
wherein the proximal portion of the cutting tip is torsionally rotated back and forth on an axis that is parallel with the shaft centerline; and
wherein the third portion balances the cutting tip to reduce lateral vibrations back and forth perpendicular to the axis.

7. The cutting tip and phacoemulsification surgical handpiece of claim 1, wherein substantially aligned comprises a range of parallel with the extended shaft centerline to 5 degrees off parallel with the extended shaft centerline.

8. The cutting tip and phacoemulsification surgical handpiece of claim 1, wherein substantially aligned with the extended shaft centerline comprises a range of parallel with the extended shaft centerline to 10 degrees off parallel with the extended shaft centerline.

9. The cutting tip and phacoemulsification surgical handpiece of claim 1, wherein the second portion forms an angle of approximately 20 degrees relative to the first portion.

10. The cutting tip and phacoemulsification surgical handpiece of claim 1, wherein the hook includes a curve that acts as a counterweight by placing tip material on one side of the extended shaft centerline with distal end tip material angled back toward the extended shaft centerline distal of the hook.

11. The cutting tip and phacoemulsification surgical handpiece of claim 1, wherein the distal portion changes directions at least three times relative to the extended shaft centerline.

12. A cutting tip and a phacoemulsification surgical handpiece, comprising:
a phacoemulsification surgical handpiece comprising a horn configured to torsionally vibrate a cutting tip at a rate of approximately 10 to 60 kHz; and
a cutting tip comprising:
a first portion comprising a straight shaft comprising a proximal portion of a cutting tip length secured in the horn of the surgical handpiece, wherein the straight shaft has a shaft centerline;
a second portion forming an angle with the first portion;
a third portion forming a hook; and
a distal end with a beveled end;
wherein the cutting tip has a diameter in a range of approximately 0.5 mm to 2 mm;
wherein the proximal portion of the cutting tip length is constrained by the horn of the surgical handpiece such that the shaft centerline of the proximal portion is aligned with an axis of rotation of the horn;
wherein the hook includes a curve that acts as a counterweight;
wherein the first portion, second portion, third portion and distal end are comprised in a single piece; and
an aspiration lumen through at least the first portion, wherein the aspiration lumen has an inner diameter between 0.001 inches and 0.09 inches;
wherein the second portion, third portion, and distal end together have an axis of rotation relative to the shaft that is substantially aligned with the extended shaft centerline when the proximal portion of the cutting tip length is torsionally vibrated by the phacoemuslfication surgical handpiece at the rate of approximately 10 to 60 kHz, on an arc with an axis of rotation that is aligned with the shaft centerline at the proximal portion.

13. The cutting tip and phacoemulsification surgical handpiece of claim 12, wherein the second portion forms an angle of approximately 20 degrees relative to the first portion.

14. The cutting tip and phacoemulsification surgical handpiece of claim 12,
wherein the proximal portion of the cutting tip is torsionally rotated back and forth on an axis that is parallel with the shaft centerline; and
wherein the third portion balances the cutting tip to reduce lateral vibrations back and forth perpendicular to the axis.

* * * * *